United States Patent [19]

Haker et al.

[11] 4,187,462
[45] Feb. 5, 1980

[54] ELECTRONIC SYSTEM FOR DETERMINING BLOOD SEDIMENTATION RATE USING A CONTINUALLY RETUNED RESONANT CIRCUIT

[75] Inventors: Rolf Haker, Frankenthal; Klaus Schräder, Heidelberg; Joachim Thiery, Mannheim, all of Fed. Rep. of Germany

[73] Assignee: Labora Mannheim GmbH fur Labortechnik, Mannheim, Fed. Rep. of Germany

[21] Appl. No.: 870,939

[22] Filed: Jan. 20, 1978

[30] Foreign Application Priority Data

Jan. 22, 1977 [DE] Fed. Rep. of Germany ....... 2702557

[51] Int. Cl.² ........................................... G01R 33/12
[52] U.S. Cl. .................................. 324/204; 324/61 P; 324/208; 324/236; 73/230 B; 73/53
[58] Field of Search ....................... 324/204, 208, 61 P, 324/236; 128/2 G; 73/53, 61, DIG. 5; 23/230 B

[56] References Cited

U.S. PATENT DOCUMENTS

| 2,102,785 | 12/1937 | Brooks | 23/258.5 |
| 2,725,782 | 12/1955 | Worley | 23/230 B |
| 3,254,527 | 5/1966 | Nöller | 128/2 G |

FOREIGN PATENT DOCUMENTS

| 690145 | 7/1964 | Canada | 324/61 P |
| 121163 | 3/1946 | United Kingdom | 324/61 P |

Primary Examiner—Robert J. Corcoran
Attorney, Agent, or Firm—Herbert L. Lerner

[57] ABSTRACT

A device for determining the blood sedimentation rate in a substantially vertical test tube, where the electrical or magnetic property of a given volume of liquid, which is changed by the settling of the erythrocytes in the test tube is measured as a function of time, by means of an oscillator with an output circuit which is completed via the column of liquid to be measured and by means of a measured-value pickup, having an output signal of which a pulse sequence of a definite frequency can be fed to a pulse counter with an indicating device.

A coil-capacitor resonant circuit is coupled inductively with its coil or capacitively with its capacitor to liquid at a definite height in the test tube. An additional coil inductively coupled to the resonant-circuit coil serves as the measuring pickup. A retuning circuit is provided for the retuning of the resonance of the tuned L-C circuit which is detuned by the lowering of the boundary layer between the erythrocyte column and the plasma in the test tube. A pulse counter connected to the retuning circuit determines the number of retuning operations which correspond to the blood sedimentation rate. The electrical or magnetic property of the liquid, which changes due to sedimentation, causes the L-C oscillation range to be detuned, and can be the dielectric constant or the permeability of the liquid volume undergoing measurement.

8 Claims, 4 Drawing Figures

ELECTRONIC SYSTEM FOR DETERMINING BLOOD SEDIMENTATION RATE USING A CONTINUALLY RETUNED RESONANT CIRCUIT

BACKGROUND OF THE INVENTION

1. Field of the Invention

This invention relates to a device for determining the blood sedimentation rate by a change in the electrical or magnetic property measured as a function of time, which change is caused by the settling of the erythrocytes in the blood.

2. Description of the Prior Art

The invention is used in medical laboratories, in clinics and by practicing physicians. Although the determination of the blood sedimentation rate is a non-specific method and permits no differential-diagnostic statements, it is extremely well suited for a first clarification of a pathological pattern and for therapy control. In the measurement of the blood sedimentation rate, use is made of the fact that normally, the erythrocytes, after being mixed with sodium citrate, if indicated, to prevent the blood from coagulating, settle from the suspension at a definite rate. For comparison, reference values have been determined. In pathological cases, the erythrocytes agglomerate more, which causes the particles to settle faster. The sedimentation reactions can vary greatly here.

Two similar methods for determining the blood sedimentation rate reaction are generally known, namely, the method named after Westergren with a determination of the height of the boundary layer at definite times, and the method named after Linzenmeier with a determination of the time of sedimentation of the boundary layer by a defined height difference. The methods are described in detail in the basic medical literature.

In one known device of the type described (French Pat. No. 2.201.762), a high-frequency square-wave pulse current is introduced by means of two electrodes connected to the oscillator via the bottom of the test tube into the adjacent volume of liquid. The amplitude change of this square-wave due to the settling of the erythrocytes into the measurement volume and the changed conductivity thereof is measured. This purpose is served by a null indicator and an appropriate reference signal. This is followed by an amplitude/frequency conversion, pulse shaping, frequency division and adaption of the pulse sequence for the succeeding counter; and the indication can be made, of course, in a manner familiar to the physician, e.g., in values for the corresponding blood sedimentation rate. The measurement in the bottom zone can be falsified greatly by dirt. The measurement signal passes through a number of circuit components in series, so that errors resulting from null drift lead to further inaccuracies. The method of measurement covers a volume of liquid, i.e., the bottom region of the test tube, in which the measuring process can be completed very fast or the hematocrit value can be reached very quickly, whereas it is the comparison of the lowering of the boundary layer between the erythrocyte column and the plasma with reference values, that is of interest to the physician, as explained above.

In other known devices, an opto-electronic measuring arrangement is run up and down along the test tube (German Published Non-Prosecuted Application No. 2 353 272; German Utility Pat. No. 1 776 034). As is well known, mechanically moved parts are trouble-prone.

The optical determination of the boundary layer is inaccurate because the latter is often not developed sharply enough. In the last-mentioned known case, however, an embodiment example is indicated, in which the light source required for the optoelectronic measurement and the photoelectric receiver can also be replaced by capacitor electrodes and a capacity measurement is to be made, as pure blood serum has a dielectric constant different from that of concentrated blood. However, it is not stated how the accurate measurement and further processing of the measured value are to be performed.

In measuring methods which operate with moving measuring devices, much time is required from the start of the measurement until a result is available. Assuming a mixture of blood with sodium citrate, a relatively flat curve is obtained for the sedimentation reaction, i.e., the function of the height of the erythrocyte column versus time. From the instant of filling up to a first point in time, the erythrocyte column is lowered slowly, due to the turbulence resulting from the filling operation. This is followed, with a gradual transition, of course, by an approximately linear region, in the center of which a second point in time can be defined. From a third point in time, there follows again a flatter region of the curve, as the packing density of the particles has become so great that it approaches the hematocrit value. According to empirical determinations, the interval from time 0 to the first point in time can be made on hour and the interval from the first to the second point in time, two hours. As the initial sedimentation rate, as described, is smaller than the sedimentation rate in the linear region and the occurring turbulence may be different and depends on further factors, there is a great spread in the so-called one-hour value. Now, it would make good sense to choose the time interval for the linear region, as this region has less interference; however, if the sedimentation is greatly accelerated, the hematocrit value can be reached substantially sooner, of course. In some cases, a planned interval of, say, two hours could be too short.

Methods are also known, in which capillary tubes or tubes provided with Heparin or another coagulation inhibitor are used in the blood sedimentation reaction (German Published Non-Prosecuted Application No. 2 137 622 and German Published Prosecuted Application No. 2 442 877). Common to both methods is the fact that dilution and prevention of the blood coagulation by liquid substances such as sodium citrate are unnecessary. In fact, using tubes coated with Heparin, for instance, simplifies the blood sedimentation determination considerably. Capillary blood can be used instead of veinous blood, and throw-away tubes can be used for mechanization. The time function of the height of the erythrocyte column has the same characteristic as the one described before, but is much more compressed in time. In particular, the time to the beginning of the linear region is substantially shorter.

SUMMARY OF THE INVENTION

An object of the present invention is to provide a relatively simple device without mechanically moving parts to achieve a largely error-free determination of the sedimentation rate of the boundary layer between the erythrocyte column and the plasma.

With the foregoing and other objects in view, there is provided in accordance with the invention a device for determining the blood sedimentation rate of erythrocytes in plasma in a substantially vertical test tube, where the electrical or magnetic property of a given volume of liquid in the test tube, changed by the sedimentation of the erythrocytes, is measured as a function of time, including a voltage-controlled oscillator with an output circuit which is completed with the volume of liquid to be measured for change in property with time, in which output circuit a tuned L-C circuit, connected to the voltage-controlled oscillator, is inductively coupled with its coil to the volume of liquid to be measured at a defined height of the test tube; a search coil inductively coupled to the coil of the tuned L-C circuit; a pulse counter connected to receive a pulse sequence of a given frequency of output of the search coil; a retuning circuit to which the additional coil is connected, is also connected with the voltage-controlled oscillator connected to the tuned L-C circuit for the intermittent retuning of the resonance of the tuned L-C circuit detuned by the blood sedimentation causing the lowering of the boundary layer between the erythrocyte column and the plasma in the test tube; the pulse counter connected to the retuning circuit determining the number of the retuning operations corresponding to the blood sedimentation rate; and a quartz-stabilized oscillator connected to the retuning circuit and the pulse counter, for forming the pulse sequence which represents the number and gets to the pulse counter when detuned, and for controlling the detuning circuit.

In accordance with the invention there is provided a device for determining the blood sedimentation rate of erythrocytes in plasma in a substantially vertical test tube, where the electrical or magnetic property of a given volume of liquid in the test tube, changed by the sedimentation of the erythrocytes, is measured as a function of time, including a voltage-controlled oscillator with an output circuit which is completed with the volume of liquid to be measured for change in property with time, in which output circuit a tuned L-C circuit, connected to the voltage-controlled oscillator, is capacitively coupled with its capacitor to the volume of liquid to be measured at a defined height of the test tube; a search coil inductively coupled to the coil of the tuned L-C circuit; a pulse counter connected to receive a pulse sequence of a given frequency of output of the search coil; a retuning circuit to which the additional coil is connected, is also connected with the voltage-controlled oscillator connected to the tuned L-C circuit for the intermittent retuning of the resonance of the tuned L-C circuit detuned by the blood sedimentation causing the lowering of the boundary layer between the erythrocyte column and the plasma in the test tube; the pulse counter connected to the retuning circuit determining the number of the retuning operations corresponding to the blood sedimentation rate; and a quartz-stabilized oscillator connected to the retuning circuit and the pulse counter, for forming the pulse sequence which represents the number and gets to the pulse counter when detuned, and for controlling the detuning circuit.

Other features which are considered as characteristic for the invention are set forth in the appended claims.

Although the invention is illustrated and described herein as embodied in device for determining the blood sedimentation rate, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which.

DETAILED DESCRIPTION OF THE INVENTION

Figures 1, 2:
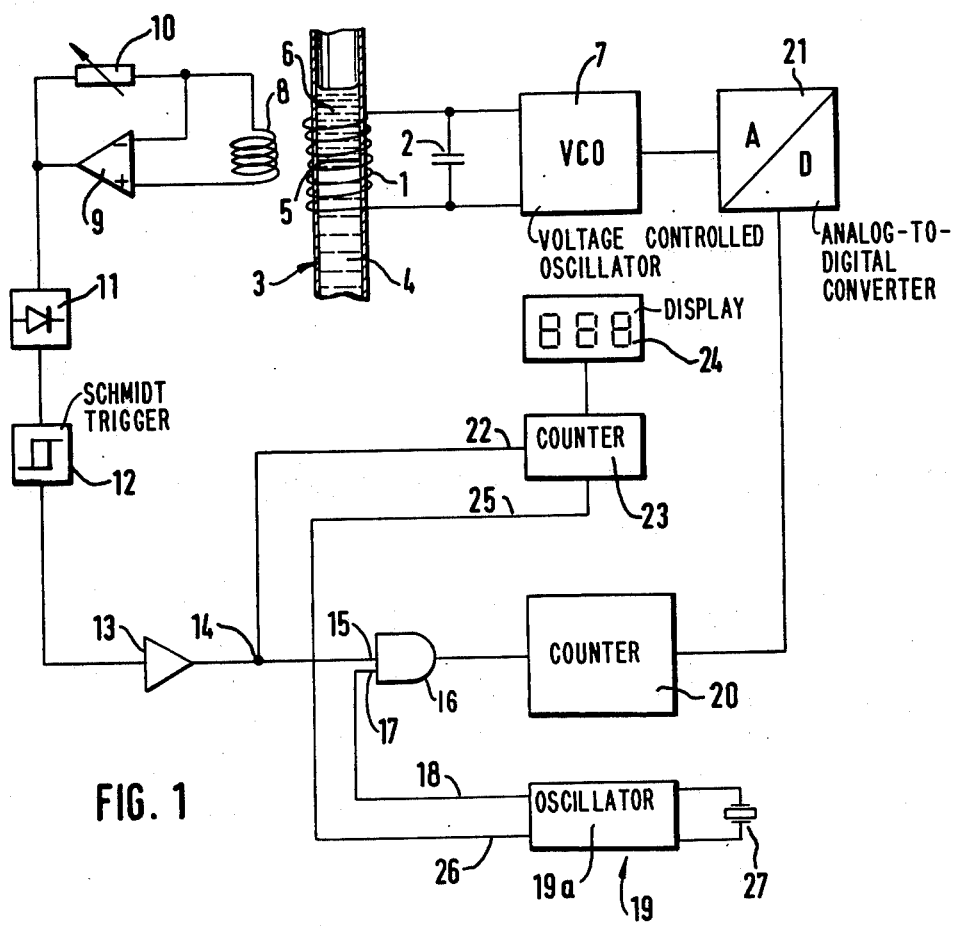
FIG. 1 shows a schematic equipment block diagram of the device for determining the blood sedimentation rate.
FIG. 2 is a specific coil arrangement for FIG. 1.

A coil-capacitor (L-C) resonant circuit is coupled inductively with its coil or capacitively with its capacitor to the volume of liquid to be measured at a definite height of the test tube. A search coil inductively coupled to the resonant-circuit coil serves as the measuring pickup. A retuning circuit is provided for the intermittent retuning of the resonance of the tuned L-C circuit with the voltage-controlled oscillator connected to the L-C circuit, which L-C circuit is detuned by the lowering of the boundary layer between the erythrocyte column and the plasma in the test tube. The pulse counter for the number of retuning operations corresponding to the blood sedimentation rate is connected to the retuning circuit. A quartz-stabilized oscillator is connected to the retuning circuit and the pulse counter, for forming the pulse sequence which represents this number and gets to the pulse counter when detuned and for controlling the retuning circuit. The electrical property, the change of which causes the L-C oscillation range to be detuned, can therefore be the dielectric constant or the permeability of the measurement volume, depending on whether the coupling is via the resonant-circuit coil or the resonant circuit capacitor.

It is generally known, as was already discussed in connection with German Utility Pat. No. 1 776 034, that erythrocytes and the plasma surrounding them have different physical properties such as a different dielectric constant and different permeability. It is also known to determine the dielectric constant or the loss factor in order to determine blood properties (German Published Non-Prosecuted Application No. 2 135 527). In the last mentioned known case, it is assumed that the dielectric properties of the blood are changed under the shear forces occurring during flow, as an alignment parallel to the flow lines or surfaces takes place and, at higher velocities, deformation. Changes of the corresponding electrical measurement values, which are determined in the known case and are due to deformation of the blood corpuscles, permits statements regarding their mechanical properties. In the known case, the blood sample is introduced into a capacitor arrangement and one of the capacitor electrodes is rotated in order to generate the mentioned shear forces in the blood. A high frequency is applied to the capacitor. The capacitor is electrically connected into a loss factor measuring bridge. The possibility is also provided for applying the electrodes and therefore, the high-frequency field, directly to a blood vessel in the body itself. To eliminate measuring inaccuracies, it is necessary to separately measure a small amount of plasma, which is separated from the blood by brief, gentle centrifuging.

In contrast thereto, the device according to the invention does not measure an electrical property or constant, but the change of the electrical or magnetic property is measured as a function of time when traversing the boundary layer.

Contrary to the device mentioned at the outset (French Pat. No. 2.201.762), the device according to the invention has the advantage that the measurement is possible in a section of the volume of liquid which is traversed by the boundary layer, i.e., the separation of the erythrocyte column and the plasma column. This facilitates comparisons between a normal case and a pathological case. The device according to the invention works more accurately because in fact, only the changes of the dielectric properties or the magnetic properties of the suspension need to be determined in a volume section which has been defined in advance and is free of turbulence and dirt. In order to obtain optimum results, the selected volume section can be chosen as large as desired. In addition, the resonance tracking by the retuning circuit is an unequivocal criterion and, because of the independent, quartz-controlled oscillator, the actually counted frequency is independent of errors of the preceding equipments. The dielectric properties change because the erythrocytes with a first dielectric constant sink down and are replaced by the remaining plasma with a second dielectric constant. Something similar is true for the permeability: Iron is adsorbed at the erythrocytes as the carriers of the hemoglobin, and it is clear that if the erythrocytes sink, to which a first permeability can be ascribed, a change of the permeability in the direction toward a smaller second permeability, i.e., toward the permeability of the plasma, takes place.

The described parameter change is automatically picked up digitally as the number of the retuning operations of the tuned L-C circuit which can be retuned to the respective resonance frequency. This measure has the advantage that in the result, an indication of the blood sedimentation values familiar to physicians can be obtained by a simple conversion or normalization, i.e., the retuning is already quantized, so that the amount of the sedimentation rate can be generated and displayed in a simple manner.

As viewed in the direction of the signal flow, the retuning circuit advantageously comprises, in common with a measurement valve transformer circuit, an amplifier connected to the additional or search coil; a rectifier; a Schmitt trigger; and an AND gate. The retuning circuit also includes a quartz-stabilized oscillator connected to the other input of the AND gate, and the AND gate is also connected to a further counter, a digital-to-analog converter and the voltage-controlled oscillator. In other words, one can also say that the instrument transformer delivers a measurement value to be processed by the components of the retuning circuit not forming part of the instrument transformer. The counter for the retuning operations is connected to a branching point ahead of the AND gate.

The capacitor of the L-C resonant circuit is preferably designed so that its electrodes partly surround the test tube in the form of two curved shells.

If the permeability is measured as a parameter, the coil of the tuned L-C circuit and the additional coil are advantageously arranged concentrically to the test tube.

Both above-mentioned measures improve the respective capacitive or inductive coupling.

The invention will be explained in greater detail referring to the embodiment examples shown in the drawings. A parallel resonant L-C circuit, consisting of a coil 1 and a capacitor 2, is inductively coupled in the embodiment example according to FIG. 1 to the test tube 3, inasmuch as the test tube 3 is inside the coil 1. In the test tube are indicated (see FIG. 2) an erythrocyte column 4, a boundary layer 5 and the plasma 6. A voltage-controlled oscillator 7, as the control element of a retuning circuit, is connected to the capacitor 2. The coil 1 is inductively coupled to an additional coil 8. The retuning circuit consists, as viewed in the direction of the signal flow, of an amplifier 9 which is connected to the additional coil 8 and is fed back via a variable resistor 10; a rectifier 11; a Schmitt trigger 12; an inverter 13; a branching point 14 which is connected to a first input 15 of an AND gate 16; a second input 17 of an AND gate 16, which input 17 is a first output 18 of a quartz-stabilized oscillator 19; a further counter 20; a digital-to-analog converter 21 and the voltage-controlled oscillator 7 at the capacitor 2. A counter 23 for the retuning operations is connected to the branching point 14 by way of its first input 22. A visual display device 24 cooperates with the counter 23. A second input 25 of the counter 23 is connected to the second output 26 of the quartz-controlled oscillator 19, composed of a frequency divider 19a.

As shown in FIG. 2, the coil arrangement in FIG. 1 is preferably constructed so that the resonant-circuit coil 1 and the additional coil 8 are concentrically disposed around the test tube 3.

If the change of the dielectric constant is measured, a tuned-circuit capacitor 102 (FIG. 3) is capacitively coupled with its electrodes 102a and 102b in the form of plate-shaped electrodes to the test tube, while the tuned-circuit coil 101 is inductively coupled only to the search coil 8. The circuit according to FIG. 1, otherwise, can be used without change.

Figure 3:
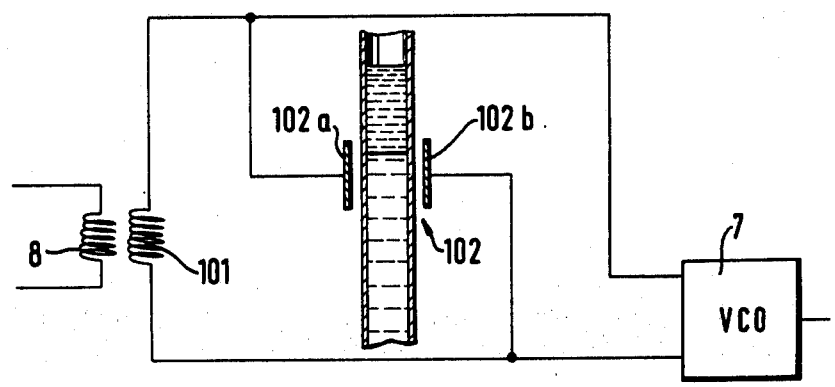
FIG. 3 is an embodiment variant of FIG. 1.
Figure 4:
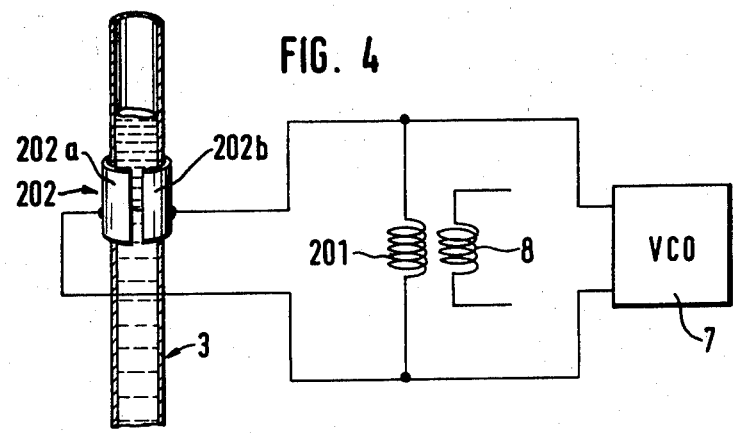
FIG. 4 is a further variant of the capacitor arrangement in FIG. 3.

The embodiment example according to FIG. 4 differs from FIG. 3 in that the electrodes 202a and 202b of the resonant-circuit capacitor 202 are curved and surround the test tube 3. Again, the tuned-circuit coil 201 is coupled only to the coil 8.

The operation of the device in accordance with the invention will be explained, referring to FIGS. 1 and 2, in the following. The test tube 3 with the blood which has been made incapable of coagulation, is inside the two coils 1 and 8. The coil 1 and the capacitor 2 together form a parallel resonant circuit, which is excited by the voltage-controlled oscillator 7.

If the coil 1 has an inductance L and the capacitor 2 a capacity C, the Thomson's equation applies for continuous oscillations:

$$w_o = 1/\sqrt{LC}$$

where $w_o$ is the angular resonance frequency.

By inserting a test tube which is filled with blood, the inductance L will change. Thus, we have for the resonant circuit:

$$w_o' = 1/\sqrt{L'C}$$

If this resonant circuit is now tuned to resonance by means of the voltage-controlled oscillator 7 and if the test tube 1 is inserted into it, a different resonance frequency will be obtained because the erythrocytes sink and the inductance $L'$ of the system is changed thereby.

The change of the resonance frequency is in direct relation to the change of the erythrocyte column 4.

Assuming that the erythrocytes settle out uniformly, the resonance frequency of the tuned circuit formed by the coil 1 and the capacitor 2 also will change uniformly. The retuning circuit serves for determining these changes. Due to the induction of the coil 1, the additional coil 8 delivers a voltage which is amplified in the amplifier 9, the gain of which can be varied via the variable feedback resistor 10. The output signal of the amplifier 9 is rectified by the rectifier 11. The rectified signal is fed to the Schmitt trigger 12, the output signal of which is inverted by the inverter 13. If the tuned circuit formed by the coil 1 and the capacitor 2 is at resonance, then a maximum voltage is induced in the additional coil 8. After amplification and rectification, this voltage causes the Schmitt trigger to assume a first defined logic state, in this case, the H-state (for positive logic, "H" corresponds here to the more positive voltage range and for negative logic, to the lower negative voltage range; for positive logic, "L" corresponds to the lower positive voltage range and for negative logic, to the higher negative voltage range). At the output of the Schmitt trigger, the decision can therefore be made as to whether or not resonance is present. If no resonance is present, the output of the Schmitt trigger 12 is at L and the output of the inverter 13 at H. Thus, also the first input 15 of the AND gate 16 is at H.

The frequency divider 19a in the quartz-stabilized ocsillator 19 receives the fixed quartz frequency f and divides it down at a given ratio. There is now a squarewave pulse sequence of given frequency at the first output 18 of the quartz-stabilized oscillator 19, which output is fed to the second input 17 of the AND gate 16.

If the tuned circuit is not at resonance, then the squarewave signals generated in the quartz-stabilized oscillator 19 will pass through the AND gate 16 and get to the bidirectional electronic counter 20. Since the pulse is present at the first input 15 of the AND gate 16, the counter 20 input is then connected to the output of the AND gate 16. The counter 20 may be a simple binary counter. Its output lines control a digital-to-analog converter 21 which generates a control voltage which is proportional to the state of the counter and is fed to the voltage-controlled oscillator 7. If the tuned circuit consisting of the coil 1 and the capacitor 2 therefore, is not at resonance, the counter 20 will increase its registration and the digital-to-analog converter 21 will generate at its output a steadily increasing voltage which causes the voltage-controlled oscillator 7 to oscillate at a steadily increasing frequency. The tuned circuit consisting of the coil 1 and the capacitor 2 will therefore oscillate, starting from a low frequency, at an increasingly higher frequency until resonance occurs. In that case, the Schmitt trigger 12 changes its state from L to H and a jump from H to L takes place at the output of the inverter 13. At this instant, the AND gate 16 cuts off and no further counting pulses get to the counter 20. The digital-to-analog converter 21 will now generate a voltage corresponding to this state which causes the voltage-controlled oscillator 7 to hold this frequency.

Due to the sedimentation of the erythrocytes, further erythrocytes will now have settled down after a short time; this changes the inductance of the coil 1 and the resonance case therefore no longer prevails. The Schmitt trigger 12 will again go from H to L and therefore, the inverter 13 from L to H. As now the one input of the AND gate 16 is again at H, counting pulses can again get at the output of the AND gate 16 to the counter 20, the count of which will be increased or decreased and thereby cause the digital-to-analog converter 21 to make a voltage change at its output which will last until resonance is again established.

A low sedimentation rate will therefore detune the tuned circuit only infrequently in a given time and therefore necessitate only infrequent retuning via the counter 20, the digital-to-analog converter 21 and the voltage-controlled oscillator 7. For a high sedimentation rate, the tuned circuit is retuned to resonance substantially more frequently. The number of changes of the Schmitt trigger 12 in a predetermined time can therefore serve as a measure for the sedimentation rate. For this purpose, the quartz time base or the quartz-stabilized oscillator 19, in addition to the counting signals available at the first output 18, generates pulses at its second output 26 which are of the order of 10 seconds. This output 26 controls the counter 23 for counting the number of retuning operations. During a time period given by the output 26, all changes of the Schmitt trigger 21 are therefore fed to the input 22 of the counter 23. The corresponding pulses are indicated, after decoding, on the display device 24. The count of the counter 23 may be printed out by means of a printer and thus record the sedimentation rate over an extended period of time.

A specific example as follows illustrates the process:

It is assumed that a test tube 3 is inserted into the coil 1 with blood known to have a low sedimentation rate. This low sedimentation rate might correspond, for instance, to a readjustment of the tuned L-C circuit of three times in 10 seconds. The Schmitt trigger 12 will therefore change its state three times. This is recognized within the predetermined time by the counter 23 and a three appears on the display device 24. If now a test tube 3 with another sample is introduced into the coil 1, with blood known to have a high sedimentation rate, then a retuning of the tuned circuit, say, twenty times in the same time interval of, for instance, 10 seconds will result. The corresponding changes of the Schmitt trigger 12 again appear on the display device 24. A calibration of the device, for instance, in mm per hour or other quantities can therefore be obtained by means of such comparison procedures, if this is considered necessary, by way of the choice of the gating time which is determined by the output 26. It can be assumed that the count which is indicated by the display device 24, and the sedimentation rate are in linear relationship to each other. After a defined short time, the measuring process is terminated.

The operation of the arrangements according to FIGS. 3 and 4, by measuring the change of the capacity of a capacitor 102a, 102b, or 202a, 202b, respectively, is in principle the same as described in connection with FIG. 1. The tuned circuit formed by the coil 101 or 201 and the capacitor 102a, 102b or 202a and 202b, respectively, is again detuned by the change of the dielectric constant due to the sedimentation of the erythrocytes. The resonance condition is again picked up by the additional coil 8 according to FIG. 1.

These examples show that the invention is not limited to a specific arrangement of the tuned-circuit coil 1 or the tuned-circuit capacitor 2. The design of the embodiment according to FIGS. 1 and 2, however, is the simplest. The device of the invention results in the following substantial advantages:

1. The result of sedimentation of the erythrocytes in blood is available after a short, predeterminable time, a few seconds after the tube containing the blood is inserted in the device. The result is an accurate value which can be compared with reference values, because one works at a defined height above the bottom of the tube, with retuning of the resonance and with an independent frequency.

2. Unequivocal results are also obtained if hemolytic serum is used.

3. Cloudy serum cannot influence the measurement cycle.

4. Only small amounts of blood need be used.

5. The course of the sedimentation action may be measured over an extended period of time and to thus record by means of a printer entirely or partially, the curve of rate of sedimentation or the corresponding values of the function of rate of sedimentation.

6. The device itself can be constructed relatively simply, as known and even standardized building blocks or units can be used, preferably integrated building blocks. Only the coil arrangement is fabricated separately.

There is claimed:

1. Electronic system for determining the blood sedimentation rate of erythrocytes in plasma in a substantially vertical test tube, where the electrical or magnetic property of a given volume of liquid in the test tube, changed by the sedimentation of the erythrocytes, is measured as a function of time, comprising a voltage-controlled oscillator with an output circuit which is coupled with the volume of liquid to be measured for change in property with time, in which output circuit a tuned L-C circuit, connected to the voltage-controlled oscillator, is inductively coupled with its coil to the volume of liquid to be measured at a defined height of the test tube; another coil inductively coupled to said coil of the tuned L-C circuit; and delivering high voltage if said L-C circuit is at resonance, and low voltage if said L-C circuit is out of resonance; a retuning circuit formed of a pulse-forming circuit and a tuning circuit connected in series, said pulse-forming circuit being connected to said other coil and delivering an output pulse of a defined logic state when said L-C circuit is out of resonance; a pulse counter connected to said pulse-forming circuit for receiving and counting said output pulses of said pulse-forming circuit, a quartz-stabilized oscillator connected to said pulse counter for delivering a quartz time base for the counting process in said counter and a pulse sequence to a first input of the tuning circuit, a second input of said tuning circuit being connected to an output of said pulse-forming circuit, and an output of said tuning circuit being connected to the input of said voltage-controlled oscillator, said tuning circuit getting pulses of said pulse sequence, when said pulse-forming circuit delivers an output pulse, and generating a voltage change, which lasts until resonance is again established, said pulse counter indicating the number of retunings of the voltage controlled oscillator within said time base and therefore the sedimentation rate of erythrocytes.

2. Electronic system for determining the blood sedimentation rate of erythrocytes in plasma in a substantially vertical test tube, where the electrical or magnetic property of a given volume of liquid in the test tube, changed by the sedimentation of the erythrocytes, is measured as a function of time, comprising a voltage-controlled oscillator with an output circuit which is coupled with the volume of liquid to be measured for change in property with time, in which output circuit a turned L-C circuit, connected to the voltage-controlled oscillator, is capacitively coupled with its capacitor to the volume of liquid to be measured at a defined height of the test tube; another coil inductively coupled to said coil of the tuned L-C circuit; and delivering high voltage if said L-C circuit is at resonance, and low voltage if said L-C circuit is out of resonance; a retuning circuit formed of a pulse-forming circuit and a tuning circuit connected in series, said pulse-forming circuit being connected to said other coil and delivering an output pulse of a defined logic state when said L-C circuit is out of resonance; a pulse counter connected to said pulse-forming circuit for receiving and counting said output pulses of said pulse-forming circuit; a quartz-stabilized oscillator connected to said pulse counter for delivering a quartz time base for the counting process in said counter and a pulse sequence to a first input of the tuning circuit, a second input of said tuning circuit being connected to an output of said pulse-forming circuit, and an output of said tuning circuit being connected to the input of said voltage-controlled oscillator, said tuning circuit getting pulses of said pulse sequence, when said pulse-forming circuit delivers an output pulse, and generating a voltage change, which lasts until resonance is again established, said pulse counter indicating the number of retunings of the voltage controlled oscillator within said time base and therefore the sedimentation rate of erythrocytes.

3. Device according to claim 1, wherein the pulse forming circuit of the retuning circuit, as viewed in the direction of the signal flow, comprises an amplifier connected to said other coil; a rectifier; a Schmitt trigger; and an inverter; and the tuning circuit of the retuning circuit comprises an AND gate, one input of which is connected to the inverter; to a second input of which the quartz-stabilized oscillator is connected; a further counter connected to the AND gate; a digital-to-analog converter connected to the further counter and to the voltage controlled oscillator, and the pulse counter for counting the number of retuning operations connected to the output of the inverter.

4. Device according to claim 2, wherein the pulse forming circuit of the retuning circuit, as viewed in the direction of the signal flow, comprises an amplifier connected to said additional coil; a rectifier; a Schmitt trigger; and an inverter; and the tuning circuit of the retuning circuit comprises an AND gate, one input of which is connected to the inverter, to a second input of which the quartz-stabilized oscillator is connected; a further counter connected to the AND gate; a digital-to-analog converter connected to the further counter and to the voltage controlled oscillator, and the pulse counter for counting the number of retuning operations connected to the output of the inverter.

5. Device according to claim 2, wherein the capacitor of the tuned L-C circuit surrounds part of the test tube with its electrodes in the form of two curved shells.

6. Device according to claim 4, wherein the capacitor of the tuned L-C circuit surrounds part of the test tube with its electrodes in the form of two curved shells.

7. Device according to claim 1, wherein the coil of the tuned L-C circuit and the other coil are arranged concentrically to the test tube.

8. Device according to claim 3, wherein the coil of the tuned L-C circuit and the other coil are arranged concentrically to the test tube.

* * * * *